(12) United States Patent
Limon

(10) Patent No.: US 6,273,910 B1
(45) Date of Patent: Aug. 14, 2001

(54) STENT WITH VARYING STRUT GEOMETRY

(75) Inventor: Timothy A. Limon, Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/266,425

(22) Filed: Mar. 11, 1999

(51) Int. Cl.$^7$ .................................................. A61F 2/06
(52) U.S. Cl. ............................................. 623/1.15; 623/1.3
(58) Field of Search .................................. 623/1.11, 1.14, 623/1.15, 1.16, 1.17, 1.3, 1.31

(56) References Cited

U.S. PATENT DOCUMENTS

| | | |
|---|---|---|
| 4,241,146 | 12/1980 | Sivachenko . |
| 4,725,334 | 2/1988 | Brimm . |
| 4,986,831 | 1/1991 | King et al. . |
| 5,019,090 | 5/1991 | Pinchuk . |
| 5,064,435 | 11/1991 | Porter . |
| 5,108,417 | 4/1992 | Sawyer . |
| 5,133,732 | 7/1992 | Wiktor . |
| 5,135,536 | 8/1992 | Hillstead . |
| 5,195,984 | 3/1993 | Schatz . |
| 5,344,425 | 9/1994 | Sawyer . |
| 5,354,308 | 10/1994 | Simon et al. . |
| 5,383,892 | 1/1995 | Cardon et al. . |
| 5,395,390 | 3/1995 | Simon et al. . |
| 5,413,597 | 5/1995 | Krajicek . |
| 5,449,373 | 9/1995 | Pinchasik et al. . |
| 5,476,506 | 12/1995 | Lunn . |
| 5,527,324 | 6/1996 | Krantz et al. . |
| 5,716,393 | 2/1998 | Lindenberg et al. . |
| 5,800,526 | * 9/1998 | Anderson et al. ................... 623/1.15 |
| 5,855,600 | * 1/1999 | Alt ...................................... 623/1.16 |
| 5,938,697 | * 8/1999 | Kilion et al. ....................... 623/1.15 |
| 6,066,168 | * 5/2000 | Lau et al. ........................... 623/1.16 |
| 6,071,298 | 6/2000 | Lashinski et al. . |
| 6,106,548 | * 8/2000 | Roubin et al. ..................... 623/1.15 |

FOREIGN PATENT DOCUMENTS

| | | |
|---|---|---|
| 0 201 466 A2 | 11/1986 | (EP) . |
| 0 541 443 A1 | 5/1993 | (EP) . |
| 0 606 165 A1 | 7/1994 | (EP) . |
| 0 688 545 A1 | 12/1995 | (EP) . |
| WO 94/17754 | 8/1994 | (WO) . |
| WO 95/23563 | 9/1995 | (WO) . |
| WO 95/26695 | 10/1995 | (WO) . |
| WO 96/09013 | 3/1996 | (WO) . |
| WO 96/26689 | 9/1996 | (WO) . |
| WO 98/48734 | 11/1998 | (WO) . |
| WO 99/02105 | 1/1999 | (WO) . |

* cited by examiner

Primary Examiner—David H. Willse
Assistant Examiner—Suzette J. Jackson
(74) Attorney, Agent, or Firm—Fulwider Patton Lee & Utecht, LLP

(57) ABSTRACT

The invention is directed to an expandable stent for implantation in a body lumen, such as an artery. The stent consists of an elongated stent body formed with a central section positioned between a proximal end section and a distal end section, each having different radial expansion characteristics. The end sections of the stent are configured to have greater resistance to radial expansion than the corresponding central section such that, when deployed with a balloon catheter device, the central section of the stent expands to an enlarged final diameter to contact the interior walls of the body lumen before or simultaneously with the end sections as fully expanded. During stent deployment, radially outwardly acting forces applied to the stent deform the U-shaped structures in the circumferential direction thereby producing radial expansion of respective cylindrical elements. Expansion of individual cylindrical elements enables respective stent sections to enlarge from a compressed first diameter to an enlarged second diameter. Size and shape of the U-shaped structures control the expansion characteristics of respective cylindrical elements. U-shaped structures designed to be more resistant to circumferential deformation are utilized to form cylindrical elements having a greater resistance to radial expansion. Cylindrical elements are strategically arranged along the axial length of the stent to form stent sections which cooperate to control radial expansion.

15 Claims, 4 Drawing Sheets

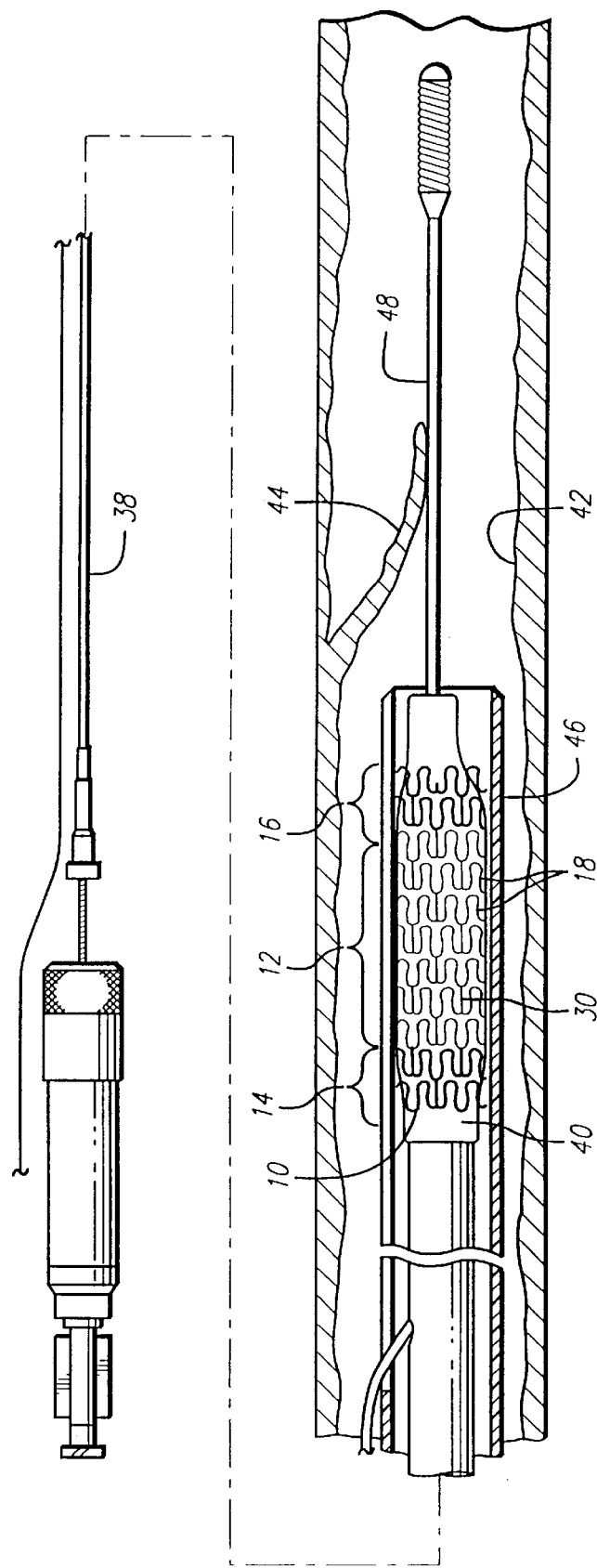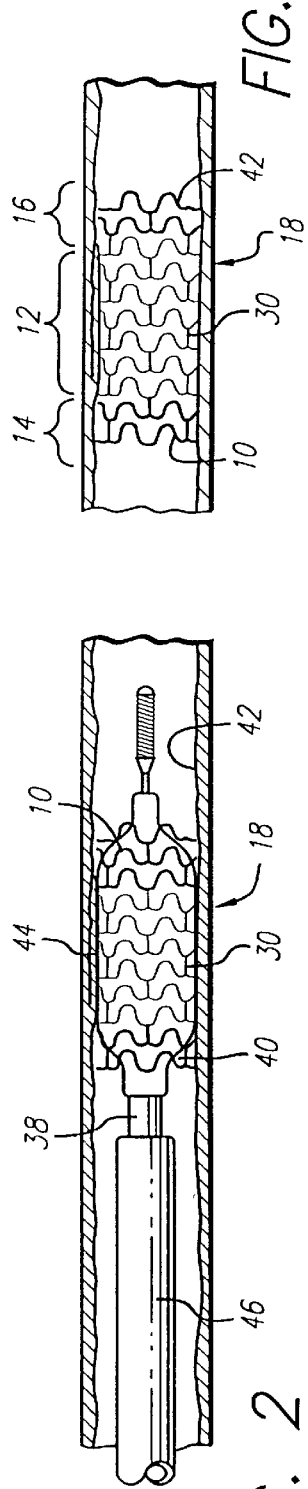

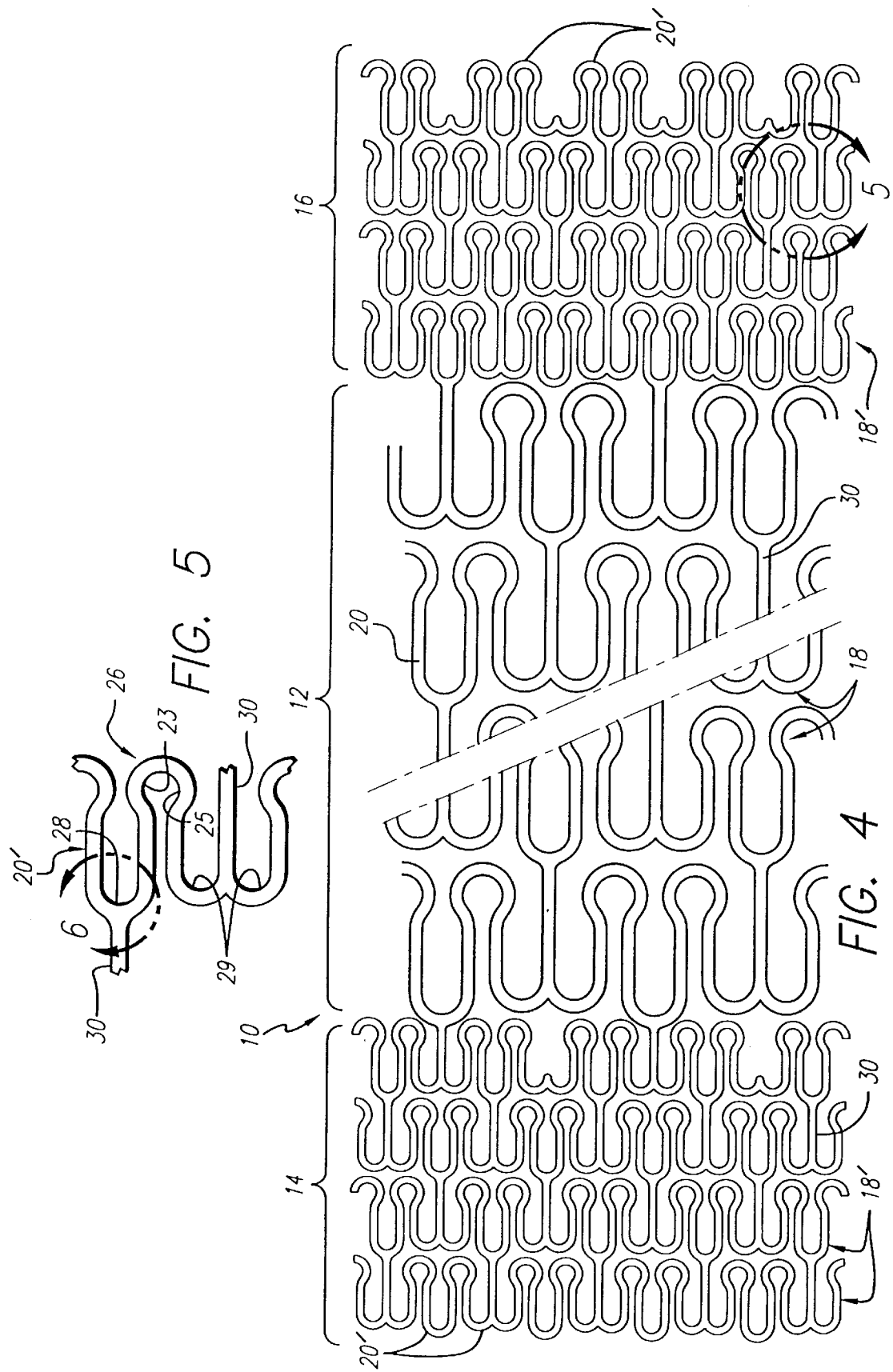

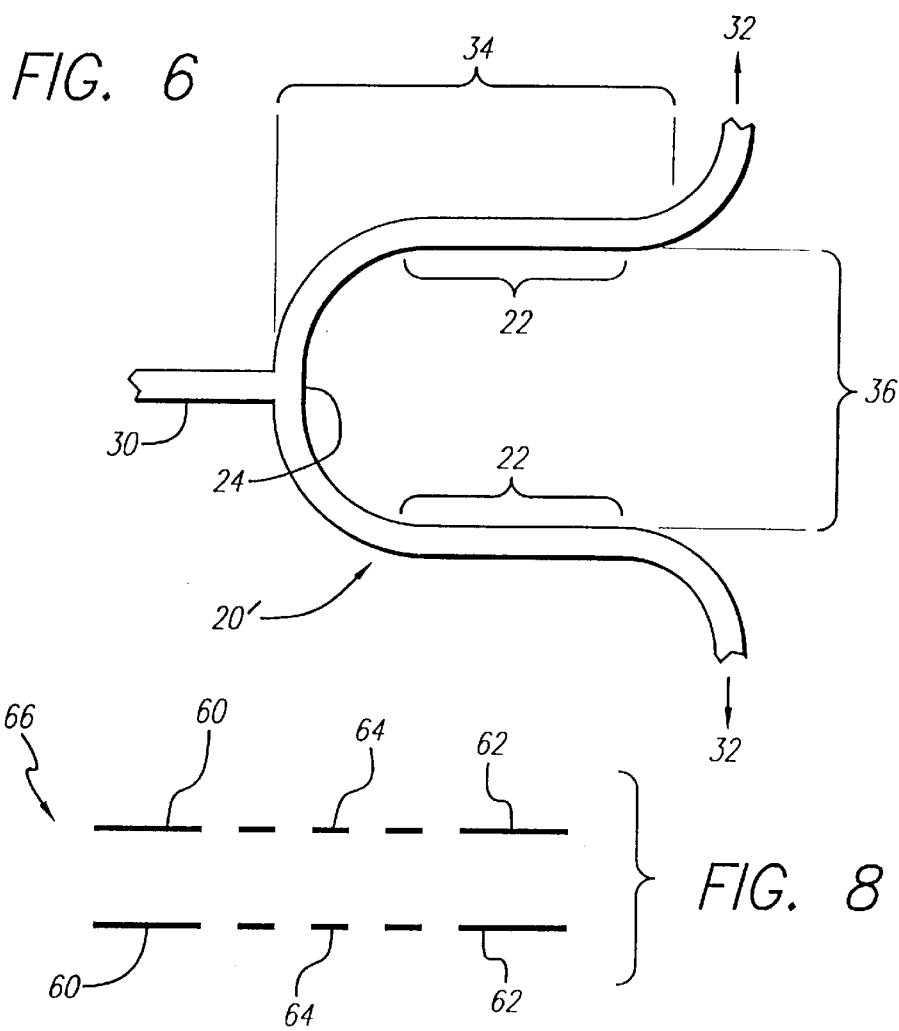
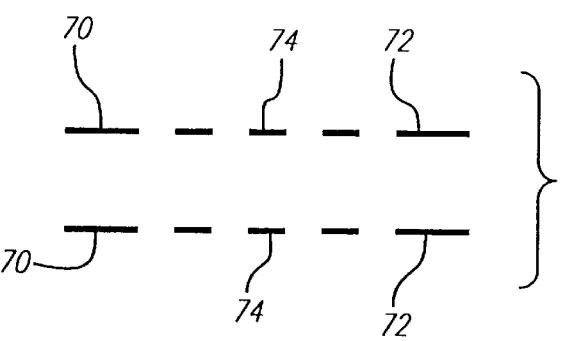
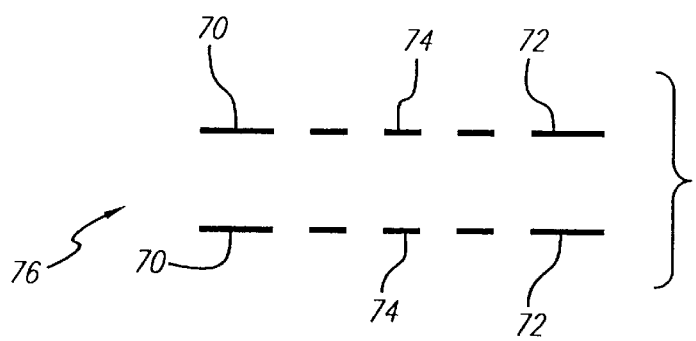
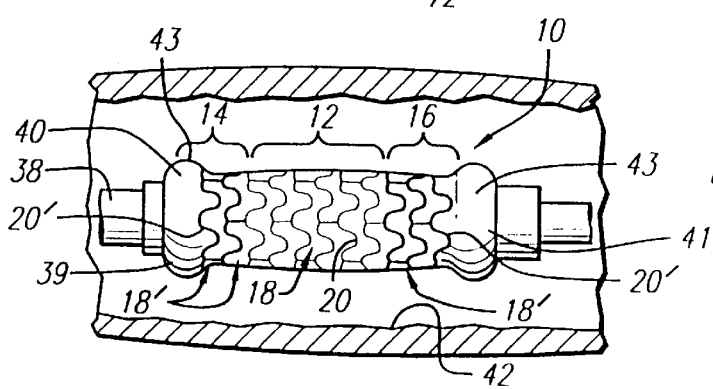

STENT WITH VARYING STRUT GEOMETRY

BACKGROUND OF THE INVENTION

This invention relates to expandable endoprosthesis devices, generally called stents, which are adapted to be implanted into a patient's body lumen, such as a blood vessel, to maintain the patency thereof. These devices are useful in the treatment and repair of atherosclerotic stenoses in blood vessels and particularly in coronary arteries.

Stents are generally cylindrically shaped devices which function to hold open and sometimes expand a segment of a blood vessel or other anatomical lumen. They are particularly suitable for use to support and hold back a dissected arterial lining which can occlude the fluid passageway there-through.

A variety of devices are known in the art for use as stents and have included balloon expandable stents made from tubes; coiled wires in a variety of patterns that are expanded after placed intraluminally on a balloon catheter; helically wound coiled springs manufactured from an expandable heat sensitive metal; and self expanding stents inserted in a compressed state and shaped in a zig zag pattern.

Although stents have been used effectively for some time, the effectiveness of a stent can be diminished if it is not properly implanted within the patient's body lumen. For example, a stent which is expanded to a desired final diameter by a balloon catheter may experience non-uniform radial expansion along its axial length due to the increased resistance to radial expansion the stent imposes about the mid-section of the balloon. Consequently, the balloon initially inflates at the proximal and distal balloon ends adjacent the balloon taper, along a path of least resistance, to form toroidally shaped lobes abutting the ends of the stent in a "dog bone" fashion. As the balloon ends over-inflate to form the characteristic "dog bone," radially outwardly acting forces from the balloon interact with the stent structure to radially expand the proximal and distal ends of the stent before the corresponding central section of the stent begins to expand. Continued uneven inflation of the balloon thereby imparts a generally hyperbolic shape to the stent structure extending along the axial length of the stent as the stent ends expand before the corresponding central section. As a result, the stent ends expand to the desired final diameter and contact the vessel wall before the corresponding center section fully expands. This non-uniform expansion often causes the stent ends to slip, relative to the underlying balloon, toward the axial center portion of the stent, thereby contracting the overall length of the deployed stent. Axial contraction of the radially enlarged stent reduces the length of the diseased vessel segment supported by deployed stent structure. Furthermore, when the respective stent ends contact the interior surface of the vessel walls, the center section must continue to expand to reach full deployment. Continued expansion of the stent center drives the stent ends radially upward and axially outward to embed deeper into the relatively soft intima of the arterial wall. This may result in damage to the ends of the stent, injury to the arterial wall, and may cause the stent to be improperly implanted.

Another difficulty encountered using prior art stents involved maintaining the radial rigidity needed to hold open the artery while at the same time maintaining the longitudinal flexibility of the stent to facilitate its delivery.

Another problem area has been the limiting range of expandability. Certain prior art stents expand only to a limited degree due to the uneven stresses created upon the stents during radial expansion. This necessitates stents with a variety of diameters thus increasing the cost of manufacture and inventory. Additionally, having a stent with a wider range of expandability allows the physician to redilate the stent if the original vessel size was miscalculated.

Another problem with the prior art stents has been contraction of the stent along its longitudinal axis upon radial expansion of the stent. This can cause placement problems within the artery during expansion such as the stent being implanted several millimeters away from the target site (i.e., the site within the vessel or artery to be treated or repaired).

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

What has been needed and heretofore unavailable is a stent which is capable of controlled radial expansion along its entire length, when deployed with a balloon-catheter, thereby allowing the central section of the stent to expand to a desired final diameter to contact the interior walls of the body lumen before the corresponding end sections fully expand, thus ensuring more uniform stent implantation. At the same time, the stent should have a high degree of flexibility so that it can be advanced through tortuous passageways and can be radially expanded over a wide range of diameters with minimal longitudinal contraction. The present invention satisfies these needs.

SUMMARY OF THE INVENTION

The present invention is directed to an expandable stent for implantation in a body lumen such as an artery. The stent consists of an elongated cylindrical stent body formed with a central section located between at least one end section having different radial expansion characteristics. The end sections of the stent are configured to have greater resistance to radial expansion than the corresponding central section such that, when deployed with a balloon catheter, the central section of the stent expands to an enlarged final diameter and contacts the interior walls of the blood vessel before the end sections are fully expanded. The stent is relatively flexible along its longitudinal axis to facilitate delivery though tortuous body lumens, but is stable enough radially, in the expanded condition, to maintain the patency of a body lumen such as an artery or other vessel when implanted therein.

The respective sections of the present invention generally consist of at least one cylindrical element which is expandable in the radial direction and arranged in alignment along a longitudinal stent axis with cylindrical elements contained in axially adjacent stent sections. The cylindrical elements are formed with U-shaped structures linked in an irregular serpentine wave pattern transverse to the longitudinal axis and contain a plurality of alternating peaks and valleys. At least one interconnecting member extends between adjacent cylindrical elements and connects them to one another. The interconnecting members unite the individual cylindrical elements to form a stent body and at the same time ensure minimal longitudinal contraction of the stent during deployment. The irregular serpentine pattern contains varying degrees of curvature in regions of the peaks and valleys and is adapted so that radial expansion of individual cylindrical elements is generally uniform around their circumferences during expansion of the stent from its contracted condition to its expanded condition.

The U-shaped structures are configured with struts and adjoining curved elements cooperating to provide curved segments which are highly flexible and which deform circumferentially upon the application of expansion forces during stent deployment. The circumferential deformation of the U-shaped structures in turn produces radial expansion of individual cylindrical elements and allows respective stent sections to expand from a first diameter to an enlarged second diameter. It will be appreciated that size, shape, cross-section, and material of the U-shaped structures may be varied to form cylindrical elements with different radial expansion characteristics. For example, U-shaped structures formed with shorter axial lengths, shorter circumferential dimensions, or wider cross-sections are more resistant to circumferential deformation than U-shaped structures having respectively longer axial lengths, larger circumferential dimensions, or more narrow cross-sections. Accordingly, U-shaped structures having greater resistance to circumferential deformation are utilized to form cylindrical elements having greater resistance to radial expansion.

The preferred stent structure of the present invention consists of a strategic arrangement of uniquely constructed adjacent cylindrical elements forming multiple stent sections which cooperate to produce an elongated cylindrical stent body capable of controlled radial expansion along its axial length. One such stent configuration consists of a proximal end section and distal end section formed with at least one cylindrical element having U-shaped structures sufficiently shorter in axial length, therefore having greater resistance to circumferential deformation, than U-shaped structures contained in respective cylindrical elements of the central section of the stent. Upon the application of radially outwardly acting expansion forces, the proximal and distal end sections are more resistant to radial expansion than the corresponding central section. Accordingly, during stent deployment, the underlying balloon of a delivery catheter will inflate, along a path of least resistance, in such a manner to thereby expand the central section of the stent to a desired final diameter slightly before or simultaneously with the corresponding stent end sections. This type of stent construction controls radial expansion and avoids the negative effects associated with balloon deployments where the characteristic "dog bone" expansion of the balloon imparts an undesirable shape to the axial length of the expanding stent structure.

Each stent section of the present invention is formed with a series of radially expandable cylindrical elements which are spaced longitudinally close enough so that small dissections in the wall of a body lumen may be pressed back into position against the lumenal wall, but not so close as to compromise the longitudinal flexibility of the stent. The irregular serpentine pattern allows for an even expansion around the circumference by accounting for the relative differences in stress created by the radial expansion of the cylindrical elements. The individual cylindrical elements may rotate slightly relative to adjacent cylindrical elements without significant deformation, cumulatively providing a stent which is flexible along its length and about its longitudinal axis, but which is still very stable in the radial direction in order to resist collapse.

The degrees of curvature along adjacent peaks and valleys formed by respective struts and curved segments defining the U-shaped structures are different in order to compensate for the stresses created during expansion of the stent so that expansion of each of the peaks and valleys is uniform relative to one another. This structure permits individual cylindrical elements to radially expand from a first smaller diameter to any number of larger second diameters since stress is distributed more uniformly along the serpentine pattern. Uniformity of stress distribution reduces the tendency of stress fractures in one particular region and allows higher expansion rates. The structure also allows the stent to expand to a greater radial expansion than heretofore was available without loss of radial strength and limited contraction of longitudinal length. The open reticulated structure of the stent allows for the perfusion of blood over a large portion of the arterial wall which can improve the healing and repair of the damaged arterial lining.

Additionally, the degree of curvature along the peaks of the U-shaped structures is different in immediately adjacent areas to compensate for the expansive properties of the valleys adjacent to it. The more uniform radial expansion of this design results in a stent which can be expanded to a much higher diameter with minimal out of plane twisting since the high stresses are not concentrated in any one particular region of the pattern, but are more evenly distributed among the peaks and valleys, allowing them to expand uniformly. Reducing the amount of out of plane twisting also minimizes the potential for aggravating thrombus formation. Preferably, the U-shaped structures of the individual cylindrical elements are in phase with each other in order to prevent the contraction of the stent along its length when it is expanded. The cylindrical elements of the stent are plastically deformed when expanded (except with NiTi alloys) so that the stent will remain in the expanded condition and therefore they must be sufficiently rigid when expanded to prevent the collapse thereof in use. With super-elastic nickel-titanium (NiTi) alloys, the expansion occurs when the stress of compression is removed so as to allow the phase transformation from austenite back to martensite and as a result the expansion of the stent.

After the stent is expanded, some of the peaks and/or valleys may tip outwardly and embed in the vessel wall. Thus, after expansion, the stent does not have a smooth outer wall surface, rather it has projections which embed in the vessel wall and aid in retaining the stent in place in the vessel after expansion.

The elongated interconnecting members which interconnect adjacent cylindrical elements should have a transverse cross-section similar to the transverse dimensions of the undulating components of the expandable cylindrical members. The interconnecting members may be formed in a unitary structure with the expandable cylindrical elements from the same intermediate product, such as a tubular element, or they may be formed independently and mechanically securing the ends of the interconnecting members to the expandable cylindrical elements. Preferably, all of the interconnecting members of a stent are joined at the valleys of the serpentine pattern of adjacent cylindrical elements which form the stent with the serpentine pattern of the cylindrical elements being in phase with one another. In this manner there is limited longitudinal shortening of the stent upon radial expansion when measured from the cylindrical elements at opposite ends of the stent.

The number and location of interconnecting members can be varied in order to develop the desired longitudinal flexibility in the stent structure both in the unexpanded as well as the expanded condition. Preferably, there are three interconnecting members between adjacent cylindrical elements. If an interconnecting member is removed, some of the highly flexible U-shaped members are freed so that they are not constrained and can more easily flex, thereby providing greater flexibility to the stent. These properties are important to minimize alteration of the natural physiology of the body lumen into which the stent is implanted and to maintain the compliance of the body lumen which is internally supported by the stent. Generally, the greater the longitudinal flexibility of the stent, the easier and the more safely it can be delivered to the implantation site.

The stent embodying features of the invention can be readily delivered to the desired lumenal location by mounting it on an expandable member of a delivery catheter, for example a balloon, and advancing the catheter-stent assembly through the body lumen to the target site. A variety of means for securing the stent to the expandable member on the catheter for delivery to the desired location is available. It is presently preferred to compress or crimp the stent onto the balloon. Other means to secure the stent to the balloon include providing ridges or collars on the inflatable member to restrain lateral movement, or using bioabsorbable temporary adhesives.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevation view, partially in section, depicting the stent embodying features of the invention which is mounted on a delivery catheter and disposed within an artery.

FIG. 2 is an elevational view, partially in section, depicting the stent of FIG. 1 expanded within a vessel to tack up a dissection.

FIG. 3 is an elevational view, partially in section, depicting the expanded stent of FIG. 2, wherein the delivery catheter is withdrawn.

FIG. 4 is an enlarged plan view of a flattened section of the stent of FIG. 1 depicting U-shaped structures linked in a serpentine pattern having peaks and valleys that form the cylindrical elements of the stent.

FIG. 5 is an enlarged partial view of a flattened section of the stent of FIG. 4 depicting the U-shaped structures having peaks and valleys which illustrate the serpentine pattern of the stent.

FIG. 6 is an enlarged partial view of a flattened section of the stent of FIG. 5 depicting the U-shaped structures having struts and curved elements.

FIG. 8 is an enlarged schematic representation of an alternative embodiment of the present invention consisting of stent sections having radial expansion characteristics that vary substantially from the stent center section to stent end sections.

FIG. 9 is an enlarged schematic representation of an alternative embodiment of the present invention consisting of stent sections having radial expansion characteristics that vary gradually from the stent center section to the stent end sections.

FIG. 10 is an enlarged elevational view, partially in section, depicting the stent of FIG. 1 expanded from a compressed first diameter to an enlarged second diameter by balloon-catheter device.

DETAILED DESCRIPTION OF THE PREFERRED EMBODIMENTS

Figure 7:
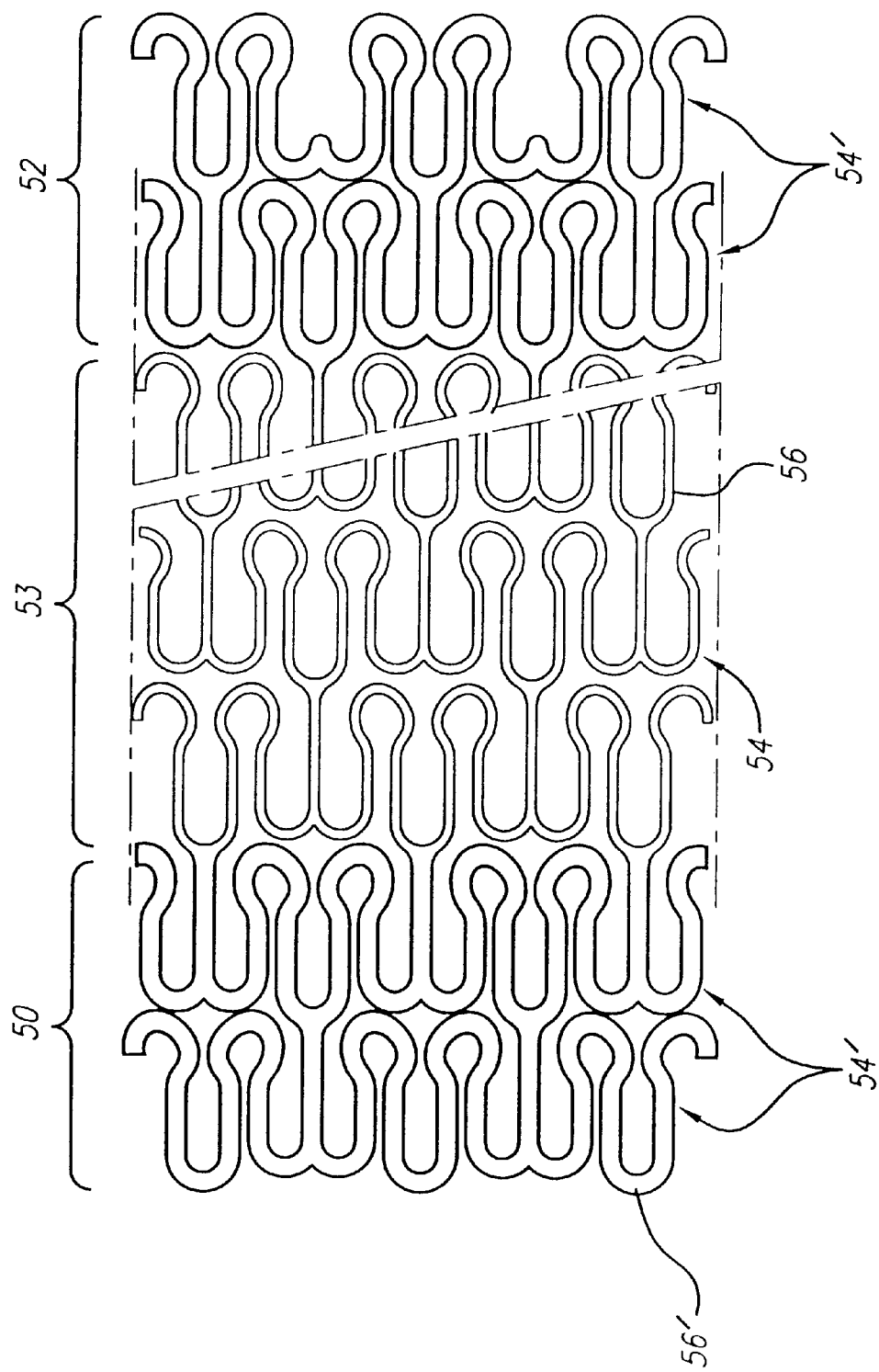
FIG. 7 is an enlarged plan view of a flattened section depicting an alternative embodiment of the present invention.

As shown in FIGS. 1 through 5, the preferred embodiment of the present invention includes elongated stent 10 consisting of central section 12, proximal end section 14, and distal end section 16 aligned along common longitudinal stent axis. Each section is formed with expandable cylindrical elements 18 having a plurality of U-shaped structures 20 linked together in a circumferential serpentine pattern. The U-shaped structures are defined by struts 22 and adjoining curved elements 24 which cooperate to produce generally U-shaped, Y-shaped and W-shaped or otherwise serpentine shaped structures having peaks 26 and valleys 28. Interconnecting members 30 extend between the axially adjacent cylindrical elements, thereby connecting them together to produce a unitary stent body. The stent remains relatively flexible as each cylindrical element is substantially independent it its ability to expand and to flex with respect to each other while interconnecting members ensure minimal longitudinal contraction during stent expansion.

Referring to FIGS. 4 through 6, U-shaped structures 20, configured with struts 22 and curved elements 24 cooperate to provide curved spring-like segments which flexibly deform circumferentially and longitudinally upon the application of expansion forces during stent deployment. The circumferential deformation of the U-shaped structures in turn produces radial expansion of individual cylindrical elements 18 and allows respective stent sections to expand from a first diameter to an enlarged second diameter.

During stent deployment, radially outwardly acting forces applied to stent 10, by for example a balloon-catheter delivery device, react about the circumference of the stent as tension forces 32 acting upon the U-shaped structures 20 of respective cylindrical elements 18. As a result, curved segments 24 deform in proportion to the tensional load to flex and expand the U-shaped structures circumferentially. Thus, circumferential deformation of the U-shaped structures in turn produces radial expansion of corresponding cylindrical elements, thereby allowing the stent sections to enlarge from an initial contracted diameter to an expanded diameter.

Size, shape, cross-section, and material of the U-shaped structures may be varied to produce different circumferential deformation characteristics. Accordingly, U-shaped structures that are designed to be more resistant to circumferential deformation are linked together to form cylindrical elements having proportionately greater resistance to radial expansion. Thus, selection of size, shape, cross-section, and material of the U-shaped structures may be utilized to tailor the radial expansion characteristics of individual cylindrical elements. Uniquely constructed cylindrical elements can then be arranged in a strategic fashion along a common longitudinal axis to form multiple stent sections having different expansion characteristics. In the preferred embodiment of the present invention, proximal end section 14, distal end section 16 and central section 12 cooperate to form stent 10 capable of radial expansion along its entire length, thereby allowing the central section of the stent to expand to a desired final diameter to contact the interior wall of the blood vessel or artery before the corresponding end sections fully expand.

Referring to FIGS. 4 and 6, cylindrical elements 18' formed with U-shaped structures 20' having shorter axial lengths 34 or shorter circumferential dimensions 36, are more resistant to radial expansion than cylindrical elements 18 formed with U-shaped structures 20 having respectively longer axial lengths or larger circumferential dimensions. In addition, U-shaped structures formed with wider cross-sections form cylindrical elements having greater resistance to radial expansion. Likewise, U-shaped structures formed from materials having a higher modulus of elasticity are more resistant to circumferential deformation than similar U-shaped structures formed from materials having a lower modulus and likewise, may be utilized to form cylindrical elements having greater resistance to radial expansion.

The stent structure of the preferred embodiment, as illustrated in FIG. 4, consists of a strategic arrangement of at least one uniquely constructed cylindrical element 18, 18' which defines a proximal end section 14, a distal end section 16 and a corresponding central section 12. In this embodiment, cylindrical elements 18' forming each end section of the stent consist of U-shaped structures 20' sufficiently shorter in axial length 34 than U-shaped structures 20 contained in cylindrical elements 18 in the corresponding central section 12 of stent 10 to produce proximal and distal end sections having greater resistance to radial expansion than the central section. The strategically arranged cylindrical elements thus cooperate to form stent 10 capable of more controlled radial expansion along its length. More specifically, during deployment the center section of the stent will expand from a compressed first diameter to an enlarged second diameter before the respective proximal and distal sections fully expand.

In an alternative embodiment, shown in FIG. 7, proximal end section 50 and distal end section 52 are formed with at least one cylindrical element 54' configured with U-shaped structures 56' having substantially wider cross sections than U-shaped structures 56 contained in cylindrical elements 54 of central section 53. As previously discussed, U-shaped structures having wider cross sections are more resistant to circumferential deformation than U-shaped structures having more narrow cross sections. Therefore, upon the application of radial expansion forces during stent deployment, cylindrical elements contained in the proximal and distal end sections of the stent have greater resistance to radial expansion than cylindrical elements contained in the central section. As a result, the central section of the stent will expand from a compressed first diameter to an enlarged second diameter to contact the interior wall of the vessel before the respective proximal and distal sections fully deploy.

In another alternative embodiment of the present invention (not shown), the proximal end section and distal end section are formed with at least one cylindrical element configured with U-shaped structures having both shorter axial lengths and wider cross sections than U-shaped structures contained in cylindrical elements of the central section. Similar to the embodiments described above, upon the application of radial expansion forces during stent deployment, cylindrical elements contained in the proximal and distal end sections of the stent have greater resistance to radial expansion than cylindrical elements contained in the central section so that the central section expands before the end sections.

It is also envisioned that the proximal and distal end sections of the stent may consist of cylindrical elements formed with material having a higher modulus of elasticity than similarly shaped cylindrical elements formed from material having a lower modulus located in a central section of the stent. Cylindrical elements of adjacent stent sections that are formed with different materials may be mechanically linked to provide a unitary stent body. It will be appreciated that stent sections formed with cylindrical elements having a higher modulus will therefore have a greater resistance to radial expansion than respective sections consisting of cylindrical elements formed with material having a lower modulus. As a result, upon the application of expansion forces during stent deployment, the central section of the stent will expand from a compressed first diameter to an enlarged second diameter to contact the interior wall of the vessel before the respective proximal and distal end sections fully deploy.

FIGS. 8 and 9 schematically depict various alternative embodiments of the present invention. The shaded blocks represent relative resistance to radial expansion of respective stent sections aligned along the axial length of the stent. Large blocks represent stent sections having greater resistance to radial expansion. Likewise, smaller blocks represent stent sections having relatively less resistance to radial expansion. Referring to FIG. 8, one such embodiment provides a stent structure where the width and/or axial length of the U-shaped structures forming respective cylindrical elements is radically altered from the central section toward the end sections of the stent. Thus resistance to radial expansion substantially increases at the proximal and distal end section 60,62 relative to central section 64 of stent 66 as shown in FIG. 8. In another embodiment, width and/or axial length of the U-shaped structures is gradually altered in adjacent cylindrical elements contained in the central section 74 toward the proximal and distal end sections 70,72, and thus resistance to radial expansion gradually increases from the center section of stent 76 toward either end section, as shown in FIG. 9.

FIG. 1 illustrates stent 10 incorporating features of the present invention which is mounted onto a delivery catheter 38. The stent generally comprises proximal end section 14, distal end section 16 and central section 12 formed with a plurality of cylindrical elements 18 interconnected by members 30 disposed between adjacent cylindrical elements. The delivery catheter has an expandable portion or balloon 40 for expanding of the stent within an artery 15 or other vessel. The artery, as shown in FIG. 1, has a dissected lining 44 which has occluded a portion of the arterial passageway.

The delivery catheter 38 onto which stent 10 is mounted, is essentially the same as a conventional balloon dilatation catheter for angioplasty procedures. The balloon 40 may be formed of suitable materials such as polyethylene, polyethylene terephthalate, polyvinyl chloride, nylon and ionomers such as Surlyn* manufactured by the Polymer Products Division of the Du Pont Company. Other polymers may also be used. In order for the stent to remain in place on the balloon during delivery to the site of the damage within artery 15, the stent is tightly crimped onto the balloon. A retractable protective delivery sleeve 46 may be provided to further ensure that the stent stays in place on the expandable portion of the delivery catheter and prevent abrasion of the body lumen by the open surface of the stent during delivery of the desired arterial location. Other means for securing the stent onto the balloon may also be used, such as providing collars or ridges on the ends of the working portion, i.e., the cylindrical portion, of the balloon.

In a preferred embodiment, the delivery of the stent 10 is accomplished in the following manner. The stent is first mounted onto inflatable balloon 40 on the distal extremity of the delivery catheter 38. The stent may be "crimped" down onto the balloon to ensure a low profile. The catheter-stent assembly can be introduced within the patient's vasculature in a conventional Seldinger technique through a guiding catheter (not shown). Guidewire 48 is disposed across the damaged arterial section with the detached or dissected lining 44 and then the catheter-stent assembly is advanced over a guidewire within the artery 42 until the stent is directly under the detached lining. The balloon of the catheter is expanded in a known manner, expanding the stent against the artery, which is illustrated in FIG. 2. While not shown in the drawing, the artery is preferably expanded slightly by the expansion of the stent to help embed the stent in the arterial wall to prevent movement. In some circumstances during the treatment of stenotic portions of an artery, the artery may have to be expanded considerably in order to facilitate blood flow.

Refering to FIG. 10, during deployment of the preferred embodiment of the present invention, balloon 40 of delivery catheter 38 tends to inflate in an uneven manner along its length due to the increased resistance to radial expansion the stent 10 imposes about the mid-section of the balloon. Consequently the balloon inflates first, along a path of least resistance, at the proximal 39 and distal 41 balloon ends, to form torodially shaped lobes 43 abutting the ends of the stent in a "dog bone" fashion. As the balloon ends over-inflate to form the characteristic "dog bone," radially outwardly acting forces from the balloon interact with the stent structure. Cylindrical elements 18' at each stent end 14, 16, formed with U-shaped structures 20' sufficiently shorter in axial dimension than U-shaped structures 20 contained in cylindrical elements 18 in the corresponding central section 12 of the stent, produce end sections and having greater resistance to radial expansion than the central section. Accordingly, the underlying balloon 40 inflates in such a manner to thereby expand the central section of the stent slightly before or simultaneously with the corresponding stent end sections. As a result, the central section expands from a first diameter to an enlarged second diameter to contact the walls of the vessel before the ends of the stent fully expand, thereby avoiding potential damage to the stent or damage to the vessel wall and ensuring proper implantation of the stent.

The cylindrical elements of the stent plastically deform when expanded so that the stent will remain in the expanded condition to provide structural support to the diseased walls of the vessel. Furthermore, the open reticulated structure of the stent allows for the perfusion of blood over a large portion of the arterial wall which can improve the healing and repair of the damaged arterial lining.

Stent 10 serves to hold open the artery 42 after catheter 38 is withdrawn, as illustrated by FIG. 3. Due to the formation of the stent from a tubular member, the undulating component of cylindrical elements 18 of the stent is relatively flat in transverse cross-section, so that when the stent is expanded, the cylindrical elements are pressed into the wall of the artery and as a result do not interfere with the blood flow though the artery. The cylindrical elements of the stent which are pressed into the wall of the artery will eventually be covered with endothelial cell growth which further minimizes blood flow interference. The serpentine pattern of the cylindrical elements provide good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery as illustrated in FIGS. 2 and 3.

In the preferred embodiment, as depicted in FIGS. 4 and 5, the stresses involved during expansion from a low profile to an expanded profile are much more evenly distributed among the various peaks 26 and valleys 28 of individual cylindrical elements. As seen in FIG. 5, a portion of cylindrical element 18 of stent 10 illustrates the irregular serpentine pattern having aplurality of peaks and valleys which aids in the even distribution of expansion forces. Interconnecting members 30 serve to connect adjacent valleys of cylindrical element as described above. During expansion, the portion 29 located in the region of the valley where the interconnecting member is connected, is the stiffest structure during deformation and the peak portion the least stiff. Thus, a larger radius at portion 39 allows it to begin expanding sooner and at a more uniform rate as compared to the expansion of peak portion 26.

Because of their design, portion 29 is the stiffest structure and peak portion 26 is the least stiff structure, which accounts for the different stresses arising during expansion. Also, the least stiff structure, peak portion 26, is positioned between portion 29 and valley portion 28 which are stiffer structures. To even out the stresses, peak portion 26 has different curvatures at regions 23 and 25. Region 23 has a larger radius than region 25 and will expand more easily. Because region 25 is adjacent the stiffer area of portion 29, both region 25 and portion 29 will expand more uniformly and more evenly distribute the expansion stresses. Further, valley portion 28 and portion 29 will expand more uniformly and more evenly distribute the expansion forces in relation to peak portion 26. Due to the novel structure as described, the shortcomings of the prior art, which include out of plane twisting of the metal, is avoided. These differing degrees of curvature along the peak portion 26 allow for the more even expansion of the cylindrical element 18 as a whole. Additionally, valley portion 29 can have differing degrees of curvature to compensate for the different stress levels during expansion. After expansion, portions of the various elements will turn outwardly, forming small projections which will embed in the vessel wall. For example, the tip of peak portion 26 tips outwardly upon expansion a sufficient amount to embed into the vessel wall and help secure the implanted stent. Upon expansion, the projecting peak 26 provides an outer wall surface on the stent that is not smooth, but instead has a plurality of projecting peaks 26 all along the outer wall surface.

While the projections assist in securing the stent in the vessel wall, they are not sharp so as to cause trauma or damage to the vessel wall.

One feature of the present invention is the capability of the stent to expand from a low-profile diameter to a diameter much greater than heretofore was available, while still maintaining structural integrity in its expanded state. Due to its structure, the stent of the present invention has an overall expansion ratio of 1 up to about 4.0 using certain compositions of stainless steel. For example, a 316L stainless steel stent of the invention can be radially expanded from a diameter of 1 unit up to a diameter of about 4.0 units, which deforms the structural members beyond their elastic limits. The stent still retains its structural integrity in the expanded state and it serves to hold open the vessel in which it is implanted. Materials other than stainless steel (316L) may give higher or lower expansion ratios without sacrificing structural integrity.

In the preferred embodiment, stent 10 is formed from a metal alloy tube such as stainless steel tubing, however, it can be made from other biocompatible materials and metal alloys including, but not limited to tantalum, NiTi, or from thermoplastic polymers. In addition, the stent structure of the present invention may be coated with biocompatible coatings. Presently, a preferred mode of making the stent is by direct laser cutting a stainless steel tube as described in commonly owned and commonly assigned U.S. Pat. No. 5,759,192 entitled METHOD AND APPARATUS FOR DIRECT LASER CUTTING OF METAL STENT, which is incorporated hererin in its entirety by reference. Other modes of making the stent of the invention are also contemplated and are known in the art.

While the invention has been illustrated and described herein in terms of its use as an intravascular stent, it will be apparent to those skilled in the art that the stent can be used in other instances in all vessels in the body. Since the stent structure of the present invention has the novel feature of controlling radial expansion along the axial length of the stent during deployment with a balloon-catheter device, it is particularly well suited for implantation in almost any vessel where such devices are used. The stent structure of the present invention is also capable of expanding to very large diameters while retaining its structural integrity. This feature, coupled with limited longitudinal contraction of the stent when it is radially expanded, provides a highly desirable support system for all vessels in the body. Other modifications and improvements may be made without departing from the scope of the invention.

What is claimed is:

1. A flexible stent for implanting in a body lumen and expandable from a contracted condition to an expanded condition, comprising:
    an elongated cylindrical body, having a central section with at least one end section, said central section and said at least one end section being constructed of a plurality of adjacent rows of cylindrical elements defined by U-shaped structures linked together in a generally serpentine wave pattern transverse to the longitudinal axis and sufficiently flexible such that upon application of radially outwardly acting forces, each of said cylindrical elements flex and expand radially;
    at least one interconnecting member extending between and connecting adjacent cylindrical elements together; and
    at least one cylindrical element of said at least one end section being formed with U-shaped structures sufficiently shorter in axial length or circumferential dimension than U-shaped structures in cylindrical elements of said central section thereby providing said at least one end section with greater resistance to radial expansion than said central section, and wherein interconnecting members extending between said U-shaped structures of such end section and said U-shaped structures of said central section are identical to interconnecting sections within either said central section or within such end section.

2. A flexible stent for implanting in a body lumen and expandable from a contracted condition to an expanded condition, comprising:
    an elongated cylindrical body, having a central section with at least one end section, said central section and said at least one end section being constructed of a plurality of adjacent rows of cylindrical elements defined by U-shaped structures linked together in a generally serpentine wave pattern transverse to the longitudinal axis and sufficiently flexible such that upon application of radially outwardly acting forces, each of said cylindrical elements flex and expand radially;
    at least one interconnecting member extending between and connecting adjacent cylindrical elements together; and
    at least one cylindrical element of said at least one end section having a greater modulus of elasticity than cylindrical elements in said central section thereby providing said at least one end section with greater resistance to radial expansion than said central section.

3. The stent of claim 1, wherein said U-shaped structure of said cylindrical elements in said at least one end section having wider cross-sections than U-shaped structures of cylindrical elements in said central section.

4. The stent of claim 1, wherein said shape and length of said U-shaped structures, and said serpentine pattern is different in adjacent cylindrical elements.

5. The stent of claim 1, wherein said stent is formed of a biocompatible material.

6. The stent of claim 1, wherein said stent is formed from a single piece of tubing.

7. The stent of claim 1, wherein said stent is coated with a biocompatible coating.

8. A flexible stent for implanting in a body lumen and expandable from a contracted condition to an expanded condition, comprising:
    an elongated cylindrical body, having a central section and at least one end section, said central section and said at least one end section being constructed of a plurality of adjacent rows of cylindrical elements defined by U-shaped structures linked together in a generally serpentine wave pattern transverse to the longitudinal axis and sufficiently flexible such that upon application of radially outwardly acting forces, each of said cylindrical elements flex and expand radially;
    at least one interconnecting member extending between and connecting adjacent cylindrical elements together; and
    at least one cylindrical element of said at least one end section being formed with U-shaped structures having wider cross sections than U-shaped structures in cylindrical elements of said central section providing said at least one end section greater resistance to radial expansion than said central section, and wherein interconnecting members extending between said U-shaped structures of such end section and said U-shaped structures of said central section are identical to interconnecting sections within either said central section or within such end section.

9. A flexible stent for implanting in a body lumen and expandable from a contracted condition to an expanded condition, comprising:
    an elongated cylindrical body, having a central section and at least one end section, said central section and said at least one end section being constructed of a plurality of adjacent rows of cylindrical elements defined by U-shaped structures linked together in a generally serpentine wave pattern transverse to the longitudinal axis and sufficiently flexible such that upon application of radially outwardly acting forces, each of said cylindrical elements flex and expand radially;
    at least one interconnecting member extending between and connecting adjacent cylindrical elements together; and
    at least one cylindrical element of said at least one end section have a greater modulus of elasticity than cylindrical elements in said central section providing said at least one end section greater resistance to radial expansion than said central section.

10. The stent of claim 8, wherein said U-shaped structures of said cylindrical elements in said end section having shorter axial lengths than U-shaped structures of cylindrical elements in said central section.

11. The stent of claim 8, wherein said shape and length of said U-shaped structures, and said serpentine pattern is different in adjacent cylindrical elements.

12. The stent of claim 8, wherein said stent is formed of a biocompatible material.

13. The stent of claim 8, wherein said stent is formed from a single piece of tubing.

14. The stent of claim 8, wherein said stent is coated with a biocompatible coating.

15. A flexible stent for implanting in a body lumen and expandable from a contracted condition to an expanded condition, comprising:

an elongated cylindrical body, having a central section and a proximal end section and a distal end section, said cental, proximal and distal sections being constructed of a plurality of adjacent rows of cylindrical elements containing U-shaped structures linked together in a generally serpentine wave pattern transverse to the longitudinal axis and flexible upon application of radially outwardly acting forces;

at least one interconnecting member extending between and connecting adjacent cylindrical elements together; and at least one cylindrical element of said proximal end section and said distal end section being formed with U-shaped structures sufficiently shorter in axial lengths or circumferential dimensions and having wider cross sections than U-shaped structures in cylindrical elements of said central section providing said proximal and distal end sections greater resistance to radial expansion than said central section thereby, upon application of expansion forces, allowing said central section to expand radially before said proximal and distal end sections, and wherein interconnecting members extending between said U-shaped structures of such end sections and said U-shaped structures of said central section are identical to interconnecting sections within either said central section or within such end sections.

* * * * *